US00RE39384E

(19) United States
(12) Reissued Patent
Buxton et al.

(10) Patent Number: US RE39,384 E
(45) Date of Reissued Patent: Nov. 7, 2006

(54) SUBSTITUTED THIAZOLIDINEDIONE DERIVATIVES

(75) Inventors: Philip Christopher Buxton, Harlow (GB); Donald Colin Mackenzie, St. Albans (GB)

(73) Assignee: SmithKline Beecham p.l.c. (GB)

(21) Appl. No.: 10/389,381

(22) Filed: Mar. 17, 2003

Related U.S. Patent Documents

Reissue of:
(64) Patent No.: 5,910,592
Issued: Jun. 8, 1999
Appl. No.: 08/892,045
Filed: Jul. 14, 1997

U.S. Applications:
(63) Continuation of application No. 08/464,990, filed on Jun. 5, 1995, now abandoned, which is a continuation of application No. 08/392,878, filed as application No. PCT/GB93/01853 on Sep. 1, 1993, now abandoned.

(51) Int. Cl.
*C07D 417/04* (2006.01)
*A61K 31/44* (2006.01)

(52) U.S. Cl. ..... 546/269.7; 514/342
(58) Field of Classification Search ..... 546/269.7; 514/342
See application file for complete search history.

(56) References Cited

U.S. PATENT DOCUMENTS

| | | | | | |
|---|---|---|---|---|---|
| 4,197,297 | A | * | 4/1980 | Weinstock | 424/244 |
| 4,287,200 | A | | 9/1981 | Kawamatsu et al. | |
| 4,340,605 | A | | 7/1982 | Kawamatsu et al. | |
| 4,376,777 | A | | 3/1983 | Kawamatsu et al. | 424/270 |
| 4,438,141 | A | | 3/1984 | Kawamatsu et al. | |
| 4,444,779 | A | | 4/1984 | Kawamatsu et al. | |
| 4,572,912 | A | | 2/1986 | Yoshioka et al. | |
| 4,582,839 | A | | 4/1986 | Meguro et al. | |
| 4,687,777 | A | | 8/1987 | Meguro et al. | |
| 4,725,610 | A | | 2/1988 | Meguro et al. | 514/369 |
| 4,873,255 | A | | 10/1989 | Yoshioka et al. | |
| 4,879,303 | A | | 11/1989 | Davison et al. | |
| 5,002,953 | A | * | 3/1991 | Hindley | 514/275 |
| 5,039,687 | A | * | 8/1991 | Effland et al. | 514/343 |
| 5,232,925 | A | | 8/1993 | Hindley | 514/272 |
| 5,478,852 | A | | 12/1995 | Olefsky et al. | 514/369 |
| 5,521,201 | A | | 5/1996 | Hindley et al. | 514/342 |
| 5,726,055 | A | | 3/1998 | Hindley et al. | 435/280 |
| 5,741,803 | A | | 4/1998 | Pool et al. | 514/342 |
| 6,288,095 | B1 | | 9/2001 | Hindley et al. | 514/367 |
| 2002/0050563 | A1 | | 5/2002 | Hindley et al. | |
| 2002/0099081 | A1 | | 7/2002 | Sasse et al. | |
| 2002/0106762 | A1 | | 8/2002 | Hindley et al. | |
| 2002/0133016 | A1 | | 9/2002 | Lynch et al. | |
| 2002/0137940 | A1 | | 9/2002 | Sasse et al. | |

FOREIGN PATENT DOCUMENTS

| | | |
|---|---|---|
| EP | 0 008 203 | 2/1980 |
| EP | 0 193 256 | 9/1986 |
| EP | 0207581 A2 | 1/1987 |
| EP | 0 306 228 | 3/1989 |
| EP | 0 419 035 | 3/1991 |
| GB | 2082584 | 3/1982 |
| GB | 87 20825 | 3/1989 |
| GB | 87 27987 | 3/1989 |
| GB | 88 02454 | 3/1989 |
| WO | WO 01/94343 | 12/2001 |
| WO | WO 01/94344 | 12/2001 |
| WO | WO 02/12231 | 2/2002 |
| WO | WO 02/12232 | 2/2002 |
| WO | WO 02/12233 | 2/2002 |
| WO | WO 02/12234 | 2/2002 |
| WO | WO 02/20517 | 3/2002 |
| WO | WO 02/20518 | 3/2002 |
| WO | WO 02/20519 | 3/2002 |
| WO | WO 02/20520 | 3/2002 |
| WO | WO 02/51839 | 7/2002 |

OTHER PUBLICATIONS

Ganong, W.F., Review of Medical Physiology, Lange Medical Publications 272 (1983).

(Continued)

*Primary Examiner*—D. Margaret Seaman
(74) *Attorney, Agent, or Firm*—Finnegan, Henderson, Farabow, Garrett & Dunner, LLP

(57) ABSTRACT

A compound of formula (I):

(I)

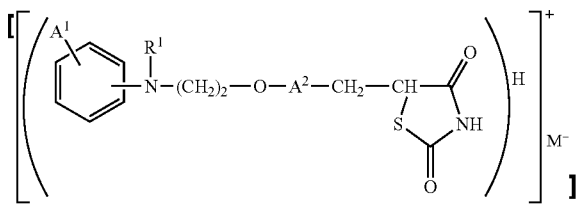

(I)

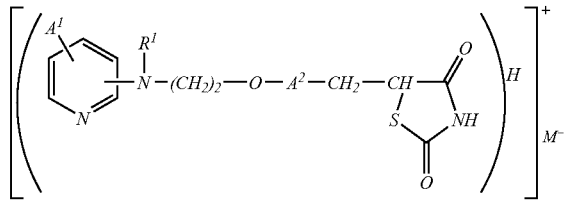

*or a tautomeric form thereof,* wherein:

$R^1$ represents a hydrogen atom, $C_{1-12}$ alkyl, $C_{1-12}$ alkoxy, $C_{1-12}$ alkylcarbonyl or aryl$C_{1-12}$ alkyl;

$A^1$ represents hydrogen or 1 to 4 optional substituents selected from the group consisting of: $C_{1-12}$ alkyl, $C_{1-12}$ alkoxy, aryl, and halogen; aryl represents phenyl or naphthyl optionally substituted with up to five groups selected from halogen, $C_{1-12}$ alkyl, phenyl, $C_{1-12}$ alkoxy, halo$C_{1-12}$ alkyl, hydroxy, nitro, $C_{1-12}$ alkoxycarbonyl, $C_{1-12}$ alkoxycarbonyl $C_{1-12}$ alkyl, $C_{1-12}$ alkoxycarbonyloxy, or $C_{1-12}$ alkylcarbonyl:

$A^2$ represents a benzene ring having 1 to 3 optional substituents selected from hydrogen, halogen, $C_{1-12}$ alkyl, $C_{1-12}$ alkoxy; and $M^-$ represents a counter-ion other than the maleate ion.

13 Claims, No Drawings

OTHER PUBLICATIONS

Sohda et al., Studies on Antidiabetic Agents. II. Synthesis of 5–[4–(1–Methylcyclohexylmethoxy)–Benzyl]Thiazolidine–2,4–Dione (ADD–3878 And Its Derivatives, *10 Chem Pharm Bull.* (Tokyo) 3580–600 (Oct. 30, 1982).
Fujita et al., Reduction of Insulin Resistance in Obese And/Or Diabetic Animals By 5–[4–(1–Methylcyclohexylmethoxy)Benzyl]–Thiazolidine–2,4–Dione (ADD–3878, U–63,287, Ciglitazone), A New Antidiabetic Agent, 32(9) *Diabetes* 804–10 (Sep. 1983).
Wilson and Grisvold's Textbook of Organic Medicine and Pharmaceutical Chemistry, pp. 590–592 8$^{th}$ Ed. 1982.
Sohda, T. et al., "Studies on Antidiabetic Agents. I. Synthesis of 5–[4–(2–Methyl–2–phenylpropoxy)–benzyl]–thiazolidine 2,4–dione (AL–321) and Related Compounds", *Chem. Pharm. Bull.,* 30(10), 3563–3573 (1982).
Chang, A.Ay., et al., "Ciglitazone, a New Hypoglycemic Agent II. Effect on Glucose and Lipid Metabolisms and Insulin Binding in the Adipose Tissue of C57BL/6J–ob/ob and —+/? Mice", *Diabetes,* 32, 839–845 (1983).
Chang, A.Y., et al., "Ciglitazone, a New Hypoglycemic Agent 3, Effect on Glucose Disposal and Gluconeogenesis in Vivo in C57BL/6J–Ob/Ob and —+/? Mice", *Diabetologia,* 25, 514–(1983).
Baba, S., et al., "New Antidiabetic Agent ADD–3878", 31 (Suppl 2), 77A (1982).
Mohrbacher, R.J., et al., "Pharmacologic Intervention in Diabetes Mellitus", Annual Reports in Medicinal Chemistry, 22, 213–222 (1987).
Sohda, T., et al., "A New Antidiabetic Agent, AD–4833, and Structure–Activity Relationships of 5–[4–(Pyridylalkoxy) benzyl]–2,4–thiazolidinediones", *J. Pharm. Sci.,* 76(11), S173 (1987).
Silverman, R.B., "Identification of the Active Part: The Pharmacophore, The Organic Chemistry of Drug Design and Drug Action", Academic Press, pp. 11–13 (1992).
Sohda, T., et al., "Studies on Antidiabetic Agents. Synthesis and hypoglycemic activity of 5–[4–(pyridylalkoxy)benzyl]–2,4–thiazolidinediones", *Arzneimittel Forschung,* 40(1), 37–42 (1990).
USP Dictionary, p. 694 (2002).
USP Dictionary, p. 911 (2002).
Sohda et al., "Studies on Antidiabetic Agents, II. Synthesis of 5–[4–(1–methylcyclohexylmethoxy)–benzyl]–thiazolidine–2,4–dione (ADD–3878) and its Derivatives", *Chemical and Pharmaceutical Bulletin,* 30(10): 3580–3600 (1982).
Berge et al., "Review Article: Pharmaceutical Salts", *Journal of Pharmaceutical Sciences,* 66(1): 1–16 (1977).
L.E. Bottiger, Ed., Carlson et al., "Pronounced Lowering of Serum Levels of Lipoprotein Lp(a) in Hyperlipidaemic Subjects Treated with Nicotinic Acid", *Journal of Internal Medicine,* 226(4): 271–76 (1989).
U.S. Appl. No. 10/030,875, filed Apr. 19, 2000, Blackler et al.
U.S. Appl. No. 10/030,323, filed Apr. 19, 2000, Blackler et al.
U.S. Appl. No. 10/048,123, filed Apr. 19, 2000, Blackler et al.
U.S. Appl. No. 10/030,877, filed Apr. 19, 2000, Blackler et al.
U.S. Appl. No. 10/019,355, filed Apr. 19, 2000, Blackler et al.
U.S. Appl. No. 10/221,686, filed Mar. 14, 2001, Craig.

* cited by examiner

SUBSTITUTED THIAZOLIDINEDIONE DERIVATIVES

Matter enclosed in heavy brackets [ ] appears in the original patent but forms no part of this reissue specification; matter printed in italics indicates the additions made by reissue.

This is a continuation of Ser. No. 08/464,990, filed Jun. 5, 1995, now abandoned, which is a continuation of Ser. No. 08/392,878, filed Mar. 3, 1995, which is a §371 of PCT/GB93/01853 filed Sep. 1, 1993.

This invention relates to certain novel compounds, to a process for preparing such compounds, to pharmaceutical compositions containing such compounds and to the use of such compounds and compositions in medicine.

European Patent Application, Publication Number 0,30628 relates to certain thiazolidinedione derivatives disclosed as having hypoglycemic and hypolipidaemic activity.

It is now surprisingly [indicate] *indicated* that a specific group of compounds from within formula (I) of EP-A-0, 306,228 have improved selectivity of action and are therefore of particular use in the treatment of Type II diabetes. These compounds are also indicated to be of particular use for the treatment and/or prophylaxis of other diseases including hyperlipidaemia, hypertension and cardiovascular disease, especially atherosclerosis. In addition these compounds are considered to be useful for treating certain eating disorders, in particular the regulation of appetite and food intake in subjects suffering from disorders associated with under-eating, such as anorexia [nervous] *nervousa*, and disorders associated with over-eating, such as obesity and anorexia bulimia.

These compounds show good aqueous stability and good stability in the solid form, certain of these compounds are indicated to be particularly stable. In addition these compounds are significantly more soluble in water than the corresponding free base.

The surprising and advantageous stability and aqueous solubility of these, compounds provides for significant formulation and bulk handling advantages.

Accordingly, the present invention provides a compound of formula (1):

(I)

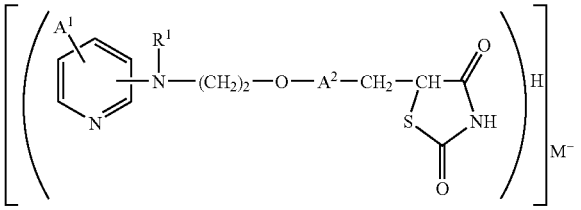

or a tautomeric form thereof and/or a pharmaceutically acceptable solvate thereof, wherein:

$R^1$ represents a hydrogen atom, an alkyl group, a acyl group, an aralkyl group, wherein the aryl moiety may be substituted or unsubstituted, or a substituted or unsubstituted aryl group, $A^1$ represents hydrogen or 1 to 4 optional substituents selected from the group consisting of alkyl, alkoxy, aryl and halogen or $A^1$ represents two substituents on adjacent carbon atoms, which substituents together with the carbon atoms to which they are attached form a substituted or unsubstituted aryl group; $A^2$ represents a benzene ring having 1 to 3 optional substituents; and $M^-$ represents a counter-ion.

Suitable counter-ions $M^-$ [include-ions] *include ions* provided by pharmaceutically acceptable acids.

A suitable source of counter-ions $M^-$ is provided by those pharmaceutically acceptable acids having a pKa in the range of from 0.1 to 4.5 and especially in the range of from [175] *1.75* to 2.5.

Favoured pharmaceutically acceptable acids include mineral acids, such as hydrobromic, hydrochloric, and sulphuric acids, and organic acids, such as methanesulphonic, tartaric and [malcic] *maleic* acids, especially tartaric and [malcic] *maleic* acid.

A preferred counter-ion is the maleate-ion HOOC.CH═CH.COO⁻.

Preferably, $A^1$ is hydrogen.

Suitable optional substituents for the moiety $A^2$ include up to three substituents selected from halogen, substituted or unsubstituted alkyl or alkoxy.

Favourably, $A^2$ represents a moiety of formula (e):

(e)

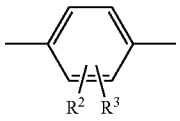

wherein $R^2$ and $R^3$ each independently represent hydrogen, halogen, substituted or unsubstituted akyl or alkoxy.

Suitably, $R^2$ and $R^3$ each independently represent hydrogen, halogen, alkyl or alkoxy.

Preferably, $R^2$ and $R^3$ each represent hydrogen.

Suitably, $R^1$ represents hydrogen, alkyl, acyl, especially acetyl, or benzyl.

Preferably, $R^1$ represents an alkyl group, for example a methyl group.

Preferably the moiety:

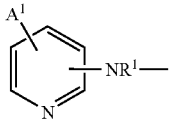

in formula (I) is a moiety of formula:

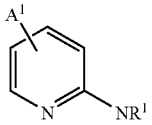

wherein $A^1$ and $R^1$ are as defined above

A preferred compound of formula (I) is 5-[4-[2-(N-methyl-N-(2-pyridyl)amino)ethoxy]benzyl]thiazolidine-2,4-dione maleic acid salt.

The compounds of formula (I) are salts. The present invention extends to all forms of such salts including those provided by association of the salting hydrogen with all possible salt forming parts of the molecule and especially that provided by association with the pyridin nitrogen.

As indicated above a compound of formula (I) may exist in one of several tantomeric forms, all of which are encompassed by the present invention. It will be appreciated that the present invention encompasses all of the isomeric forms of the compounds of formula (I) and the pharmaceutically acceptable salts thereof, including any stereoisomeric forms thereof, whether as individual isomers or as mixtures of isomers.

When used herein the term [‘aylr’] *‘aryl’* includes phenyl and naphthyl optionally substituted with up to five, preferably up to three, groups selected from halogen, alkyl, phenyl, alkoxy, haloalkyl, hydroxy, nitro, alkoxycarbonyl, aloxycarbonylalkyl, alkylcarbonyloxy, or alkylcarbonyl groups.

When used herein the term ‘halogen’ refers to fluorine, chlorine, bromine and iodine; preferably chlorine.

Suitable alkyl groups, including alkyl groups per se and alkyl groups that form part of other groups such as alkoxy groups, are $C_{1-12}$ groups having straight or branched carbon chains, especially $C_{1-6}$ alkyl groups e.g. methyl, ethyl, n-propyl, iso-propyl, n-butyl, isobutyl or tert-butyl groups.

Suitable substituents for any alkyl group include those indicated above in relation to the term “aryl”.

Suitable acyl groups include alkylcarbonyl groups.

Suitable pharmaceutically acceptable solvates include hydrates.

In a further aspect the present invention also provides a process for the preparation of a compound of formula (I), or a tautomeric form thereof, and/or a pharmaceutically acceptable solvate thereof, which process comprises reacting a compound of formula (II):

(II)

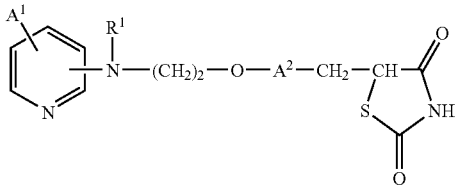

wherein $R^1$. $A^1$ and $A^2$ are as defined in relation to formula (I) with a source of above defined counter-ion $M^-$; and thereafter if required preparing a pharmaceutically acceptable solvate thereof.

A suitable source of a counter-ion $M^-$ is a pharmaceutically acceptable acid.

A suitable source of counter-ions includes pharmaceutically acceptable acids having a $pK_a$ in the range of from 1.5 to 4.5; especially in the range of from 1.75 to 2.5.

Favoured pharmaceutically acceptable acids include mineral acids, such as hydrobromic, hydrochloric and sulphuric acids, and organic acids, such as methanesulphonic, tartaric and maleic acids.

A preferred source of a counter-ion is maleic acid.

The reaction between the compound of formula (I) and the source of counter-ion $M^-$ is generally carried out under conventional salt forming conditions, for example by admixing the compound of formula (I) and the source of counter-ion $M^-$, suitably in approximately equimolar amounts but preferably using a slight excess of the source of counter-ion $M^-$, in a solvent, generally a $C_{1-4}$ alkanolic solvent such as ethanol, at any temperature which provides a suitable rate of formation of the required product, generally at an elevated temperature for example at the reflux temperature of the solvent and thereafter crystallising the required product.

Pharmaceutically acceptable solvates of the compound of formula (I) may be prepared using conventional chemical procedures.

The compound of formula (II) may be prepared according to methods disclosed in EP-A-0306228.

Suitable sources of counter-ion are known commercially available sources, such as [malcic] *maleic* acid, or the required source may be prepared according to known procedures.

Where appropriate the isomeric forms of the compounds of formula (I) and the pharmaceutically acceptable salts thereof may be prepared as individual isomers using conventional chemical procedures.

The stability of the compounds of the invention may be determined using conventional quantitative analytical methods: For example the stability of the compounds in the solid form may be determined by using accelerated stability test such as differential scanning calorimetry (I) (DSC), thermogravimetric analysis (TGA) and isothermal testing at elevated temperatures including conventional storage test wherein the test compounds are stored under controlled conditions of temperature and humidity over known periods of time. Quantitative analysis of the test compounds, against appropriate reference standards before, during and after the storage period allows the stability of the test compound to be determined.

As stated the compounds of the invention are significantly more soluble in water than the corresponding free base. Thus a convenient method for [determing] *determining* the stability of the compounds of the invention in aqueous solution involves determining the degree of precipitation of the parent free base from an aqueous solution of the test compound at known conditions of temperature and over known periods of time. We have found that the compounds of formula (I) show good aqueous stability. In particular the compounds of formula (I) wherein M– represents maleate or [tarrate] *tartrate* are particularly stable in aqueous solution. Most surprisingly, the compounds of formula (I) wherein $M^-$ represents a maleate-ion, $HOOC.CH{=}CH.COO^-$, were found to be particularly stable in aqueous solution.

The quantitative analysis of the test compounds in the above mentioned tests may be carried out using conventional methods, generally chromatographic methods such as high pressure liquid chromatography.

As mentioned above the compounds of the invention are indicated as having useful therapeutic properties:

The present invention accordingly provides a compound of formula (I), and/or a pharmaceutically acceptable solvate thereof[.], for use as an active therapeutic substance.

Thus the present invention provides a compound of formula (I), or a tautomeric form thereof and/or a pharmaceutically acceptable solvate thereof, for use in the treatment of and/or prophylaxis of hyperglycaemia.

In a further aspect the present invention also provides compound of formula (I)[.], or a tautomeric form thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable solvate thereof for use in the treatment of hypertension, cardiovascular disease and certain eating disorders.

Cardiovascular disease includes in particular atherosclerosis.

Certain eating disorders include in particular the regulation of appetite and food intake in[,] subjects suffering from disorders associated with under-eating, such as anorexia nervosa and disorders associated with over-eating, such as obesity and anorexia bulimia.

A compound of formula (I), or a tautomeric form thereof and/or a pharmaceutically acceptable solvate thereof, may be administered per se or, preferably as a pharmaceutically composition also comprising a pharmaceutically acceptable carrier.

Accordingly, the present invention also provides a pharmaceutical composition comprising a compound of formula (I), or a tautomeric form thereof, a pharmaceutically acceptable solvate thereof, and a pharmaceutically acceptable carrier therefor.

As used herein the term 'pharmaceutically acceptable[']' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant flavourant or other conventional adjuvant.

Typical carriers include, for example, microcrystalline cellulose, starch, sodium starch glycollate[.], polyvinylpyrrolidone, polyvinylpolypyrrolidone, magnesium[.] stearate or sodium lauryl sulphate.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The [.] present invention further provides a method for the treatment and/or prophylaxis of hyperglycaemia in a human or non-human mammal which comprises administering an effective, non-toxic, amount of a compound of formula (I), or a tautomeric form thereof and/or a pharmaceutically acceptable solvate thereof to a [hyperglycaemia] *hyperglycemic* human or non-human mammal in need thereof.

The present invention further provides a method for the treatment of hyperlipidaemia in a human or non-human mammal, which comprises administering an effective, non toxic, amount of a compound of formula (I), or a tautomeric form thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of formula (I), or a tautomeric form, thereof and/or a pharmaceutically acceptable solvate thereof, may be taken in doses, such as those described above, one in six times a day in a manner such that the total daily dose for a 70 kg adult will generally be in the range of from 0.1 to 6000 mg, and more usually about 1 to 1500 mg.

In the treatment and/or prophylaxis of hyperglycaemic non human mammals, especially dogs, the active ingredient may be administered by mouth usually once or twice a day and in an amount in the range of from about 0.025 mg/kg to 25 mg/kg, for example 0.1 mg/kg to 20 mg/kg. Similar dosage regimens are suitable for the treatment and/or prophylaxis of [hyperlipidaemic] *hyperlipidaemia* in non-human mammals.

The dosages regimens for the treatment [or] *of* hypertension cardiovascular disease and eating disorders will generally be those mentioned above in relation to hyperglycaemia.

In a further aspect the present invention provides the use of a compound of formula (I), or a tautomeric form thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable solvate thereof, for the manufacture of a medicament for the treatment and/or prophylaxis of hyperlipidaemia, hypertension, cardiovascular disease or certain eating disorders.

The following Example illustrates the invention but does not limit it in any way.

EXAMPLE 1

5-[4-[2-(N-Methyl-N-(2-pyridyl)amino)ethoxy]benzyl] thiazolidine-2,4-dione, maleic acid salt 5-[4-[2-(N-Methyl-N-(2-pyridyl)amino)ethoxy]benzyl] thiazolidine-2,4 dione (470 g) and maleic acid (137 g) were dissolved in ethanol (41) at boiling. The hot solution was filtered via diatomaceous earth and was then allowed to cool slowly with gentle agitation. After leaving in a refrigerator at 0–5° C. for several hours, the maleate salt was filtered off, washed with ethanol and dried in vacuo at 50° C. to give 446 g (73%) of product, m.p 120–121° C.

1H NMR δ ($d_6$-DMSO): 3.0–3.35 (2H, complex); 3.10 (3H, s); 3.95 (2H, t); 4.15 (2H, t); 4.85 (1H, complex): 6.20 (2H, s); 6.65 (1H, t); 6.85 (3H, complex); 7.15 (2H, d) 7.65 (1H, t); 8.05 (1H, complex); 11.85–12.1 (1H, broad, exchanges with $D_2O$)

A very broad signal was observed in the range 2–5 ppm which is thought to be due to residual water from the solvent and the exchangeable carboxylic acid protons.

[EXAMPLE2] *EXAMPLE 2*

5-[4-[2-(N-Methyl-N-(2-pyridyl)amino)ethoxy]benzyl] thiazolidine-2,4-dione, maleic acid salt 5-[4-[2-(N-Methyl-N-(2-pyridyl)amino)ethoxy]benzyl] thiazolidine-2,4-dione, maleic acid salt (294.6 g, 0.825 M) and maleic *acid* (95.8 g 0.825 m) were stirred in refluxing ethanol (2.71) until all the solid had dissolved. Decolourising charcoal was added and the hot solution filtered through celite, allowed to cool to room temperature with stirring. After cooling in a refrigerator at 0–5° C. for several hours, the title compound was filtered, collected and dried at 50° C. under vacuum overnight to give 364.1 g (87%) of product, m.p. 119–119.5° C.

The 1H NMR spectra was as for Example 1.

We claim:

1. A compound [of formula (I):

(I)

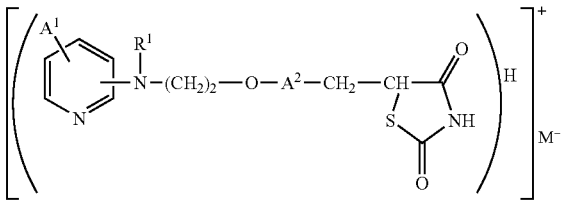

or a tautomeric form thereof, wherein:

$R^1$ represents a hydrogen atom, $C_{1-12}$ alkyl, $C_{1-12}$ alkoxy, $C_{1-12}$ alkylcarbonyl or aryl$C_{1-12}$ alkyl;

$A^1$ represents hydrogen or 1 to 4 optional substituents selected from the group consisting of: $C_{1-12}$ alkyl, $C_{1-12}$ alkoxy, aryl and halogen;

aryl represents phenyl or naphthyl optionally substituted with up to five groups selected from halogen, $C_{1-12}$ alkyl, phenyl, $C_{1-12}$ alkoxy, halo$C_{1-12}$ alkyl, hydroxy, nitro, $C_{1-12}$ alkoxycarbonyl, $C_{1-12}$ alkoxycarbonyl, $C_{1-12}$ alkoxycarbonyloxy, or $C_{1-12}$ alkylcarbonyl;

$A^2$ represents a benzene ring having 1 to 3 optional substituents selected from hydrogen, halogen, $C_{1-12}$ alkyl, $C_{1-12}$ alkoxy; and $M^-$ represents a counter-ion other than the maleate ion]

*which is 5-[4-[2-(N-methyl-N-(2-pyridyl)amino)ethoxy]benzyl]thiazolidine-2,4-dione tartaric acid salt or a tautomer of 5-[4-[2-(N-methyl-N-(2-pyridyl)amino)ethoxy]benzyl]thiazolidine-2,4-dione tartaric acid salt.*

2. A process for the preparation of a compound [of formula (I)] according to claim 1[, or a tautomeric form thereof,] which process comprises reacting [a compound of formula (II):

(II)

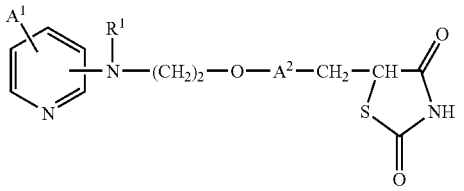

wherein $R^1$, $A^1$, and $A^2$ are as defined in relation to formula (I) in claim 1, with a source of counter-ion $M^-$ which is defined in relation to formula (I), as defined in claim 1]

*5-[4-[2-(N-methyl-N-(2-pyridyl)amino)ethoxy]benzyl]thiazolidine-2,4-dione or a tautomeric form thereof with a source of tartarate ion.*

*3. The compound according to claim 1, wherein the salt is in a solid form.*

*4. A pharmaceutical composition comprising a compound according to claim 1 and at least one pharmaceutically acceptable carrier.*

*5. The pharmaceutical composition according to claim 4 comprising an individual isomer of 5-[4-[2-(N-methyl-N-(2-pyridyl)amino)ethoxy]benzyl]thiazolidine-2,4-dione tartaric acid salt or a tautomer of 5-[4-[2-(N-methyl-N-(2-pyridyl)amino)ethoxy]benzyl]thiazolidine-2,4-dione tartaric acid salt.*

*6. The pharmaceutical composition according to claim 4 comprising a mixture of isomers of 5-[4-[2-(N-methyl-N-(2-pyridyl)amino)ethoxy]benzyl]hiazolidine-2,4-dione tartaric acid salt or a tautomer of 5-[4-[2-(N-methyl-N-(2-pyridyl)amino)ethoxy]benzyl]thiazolidine-2,4-dione tartaric acid salt.*

*7. The pharmaceutical composition according to any one of claims 4 to 6, wherein the composition is in a form suitable for oral administration.*

*8. The pharmaceutical composition according to claim 7, wherein the form is chosen from tablets, capsules, and powders.*

*9. The pharmaceutical composition according to claim 7, wherein the form is a tablet.*

*10. The pharmaceutical composition according to claim 4, wherein the composition is in a form suitable for injection.*

*11. The pharmaceutical composition according to claim 4, wherein the composition is in a form suitable for percutaneous absorption.*

*12. The pharmaceutical composition according to claim 4, wherein the at least one pharmaceutically acceptable carrier is chosen from microcrystalline cellulose, starch, sodium starch glycollate, polyvinylpyrrolidone, polyvinylpolypyrrolidone, magnesium stearate, and sodium lauryl sulphate.*

*13. The pharmaceutical composition according to claim 4, wherein the at least one pharmaceutically acceptable carrier comprises a diluent, filler, disintegrant, wetting agent, lubricant, colourant, flavourant, or adjuvant.*

* * * * *